United States Patent [19]

Silver et al.

[11] Patent Number: 4,934,816
[45] Date of Patent: Jun. 19, 1990

[54] LASER ABSORPTION DETECTION ENHANCING APPARATUS AND METHOD

[75] Inventors: Joel A. Silver; Alan C. Stanton, both of Sante Fe, N. Mex.

[73] Assignee: Southwest Sciences, Incorporated, Sante Fe, N. Mex.

[21] Appl. No.: 196,135

[22] Filed: May 18, 1988

[51] Int. Cl.$^5$ ...................... G01N 21/17; G01N 21/35
[52] U.S. Cl. .................... 356/409; 250/343; 356/437; 356/440
[58] Field of Search ............... 356/409, 437, 439, 440, 356/446; 250/343, 576

[56] References Cited

U.S. PATENT DOCUMENTS

| | | |
|---|---|---|
| 3,500,241 | 3/1970 | Bjorkholm . |
| 3,533,014 | 10/1970 | Coccoli et al. ................. 356/350 X |
| 3,573,654 | 4/1971 | Smiley . |
| 3,609,389 | 9/1971 | Bjorkholm ......................... 307/88.3 |
| 3,931,592 | 1/1976 | Hughes . |
| 4,216,440 | 8/1980 | Rahn . |
| 4,268,800 | 5/1981 | Johnston, Jr. et al. . |
| 4,395,769 | 7/1983 | Damen et al. .......................... 372/7 |
| 4,556,959 | 12/1985 | Scott et al. ............................ 372/20 |
| 4,684,258 | 8/1987 | Webster ............................. 356/409 |

OTHER PUBLICATIONS

"Brewster-Plate Spoiler: a Novel Method for Reducing the Amplitude of Interference Fringer that Limit Tunable-Laser Absorption Sensitivities," *J. Opt. Soc Am. B.*/vol. 2, No. 9/Sep. 1985, by Christopher R. Webster.
A Versatile Technique for Reducing Optical Interference Fringes in Laser Absorption Experiments, retitled "Optical Interference Fringes in Laser Absorption Experiments", *Appl. Opt.* 27, 1914 (1988) by Silver and Stanton.
"Sensitivity Limits of Tunable Diode Laser Spectrometer, with Application to the Detection of NO$_2$ at the 100-ppt Level", *Appl. Opt.* 19 3349 (1980) by Reid et al.
"Harmonic Detection with Tunable Diode Lasers-Two-Tone Modulation", *Appl. Phys.* B 29, 279 (1982) by Cassidy et al.

*Primary Examiner*—Vincent P. McGraw
*Attorney, Agent, or Firm*—Robert W. Weig; Deborah A. Peacock

[57] ABSTRACT

The disclosure relates to an apparatus and method for increasing the sensitivity of laser absorption detection of gas phase atoms and molecular species within a gaseous medium. An active optical element in a laser absorption detection system is translationally (longitudinally) vibrated a selected amplitude along the optical axis and at a desired frequency to eliminate fringes produced by interference fringe producing optical elements. The vibration frequency is preferably asynchronous with other modulation frequencies in the system.

12 Claims, 3 Drawing Sheets

LASER ABSORPTION DETECTION ENHANCING APPARATUS AND METHOD

GOVERNMENT RIGHTS

This invention was made with government support under contract No. ISI-8660775 awarded by the National Science Foundation. The Government has certain rights in this invention.

BACKGROUND OF THE INVENTION

Many spectroscopic measurement methods employing lasers have been developed for the sensitive detection of gas phase species. A common method is laser absorption, in which a laser beam is transmitted through a sample medium and the fraction of the light which is absorbed by gases contained in the sample is measured. Through knowledge of the absorption spectra of different gases, the concentration of particular gases which absorb light at the laser wavelength can be determined. Since the fraction of laser light which is absorbed is proportional to the concentration of the absorbing gas, the sensitivity for measuring small gas concentrations can be improved by removing any sources of noise or interference which otherwise restrict the minimum amount of absorption that can be measured. Laser absorption methods have many applications in laboratory research, measurement of trace species in the natural or polluted atmosphere, detection of gaseous impurities, toxic gas monitoring, in situ monitoring of combustion or other chemical processes, etc.

Optical interference fringe effects impose severe sensitivity restrictions on measurements of gas phase species using laser absorption methods. Typically, fringes, which manifest themselves as interference fringes in transmission spectra, are created by the scattering of coherent laser light from optical surfaces, such as those on mirrors, lenses, windows, and the like, disposed within the light's path. Fringes occur when light which is scattered from an optical surface is scattered again such that it reaches the optical detector and interferes with the primary transmitted beam. Fringes are especially common in systems using multiple pass cells. These cells are used to enhance the sensitivity of absorption measurements by greatly extending the path length over which absorption occurs, but they also increase the likelihood of fringe generation due to multiple reflections from mirror surfaces within the cell, thereby negating any advantage gained by increased path length.

The sensitivity of a laser absorption measurement system can be described as the minimum amount of laser absorption which can be measured. For example, with laser power levels in the range of 0.01 to 1.0 milliwatt (mW), which is typical of mid- or near-infrared diode lasers, and commercially available infrared detectors, detector noise-limited sensitivity is generally equivalent to approximately $10^{-6}$ or $10^{-7}$ fractional absorption. In multiple pass cells, the fringe amplitudes typically generated are many orders of magnitude larger than the detector noise level. For example, using a conventional "White cell" multiple pass design, Reid, et al., (J. Reid, M. El-Sherbiny, B. K. Garside, and E. A. Ballik, "Sensitivity Limits of a Tunable Diode Laser Spectrometer, with Application to the Detection of $NO_2$ at the 100-ppt Level," Appl. Opt. 19, 3349 (1980)) have reported fringe amplitudes typically greater than $10^{-3}$ equivalent absorption. In Herriott cells, when used with single frequency diode lasers, as disclosed in Silver and Stanton, "Optical Interference Fringe Reduction in Laser Absorption Experiments" (Appl. Opt., in press), fringe amplitudes usually range from about one to five $\times 10^{-4}$ equivalent absorption. Thus, the presence of the fringes seriously degrades the sensitivity, potentially by a factor of 1000 or more. In many applications, the fringes produced can render laser absorption instrumentation essentially useless. For example, in measurement of trace atmospheric species, it is important to measure many gases that are present at concentrations of less than one part-per-billion (ppb). Diode laser instrumentation, when used with an absorption path length of greater than 1 or 2 meters, as can be easily attained with standard multipass cell designs, has the potential of sub-ppb detection sensitivity if it can be operated near the detector noise limit. Therefore, the presence of interference fringes can severely restrict the application of such instrumentation by limiting detection sensitivity to concentrations near the part-per-million, rather than the desired part-per-billion level.

Fringe filtering has been conducted using both post measurement digital filtering of data and active electronic filtering as data is generated. Unfortunately, the characteristic frequency (free spectral range) of the fringes is often similar to the frequency widths of the gas absorption features under study, so that filtering techniques cannot adequately discriminate between absorption lines and interference fringes. Assume the free spectral range is $c/2L\eta$ where c is the speed of light, $\eta$ is the index of refraction of the gaseous medium in the absorption path ($\eta \approx 1$), and L is the distance between the optical surfaces which give rise to the interference effects. In multiple pass cells, fringes typically arise due to light scattered from the same mirror surface on succeeding passes, so that $L=2d_s$, where $d_s$ is the separation distance between the mirrors forming the multipass cell. For mirror separations of 0.25 to 2.5 meters, a range of experimentally convenient cell lengths for laboratory applications, the corresponding characteristic fringe spacing ranges from 300 MHz to 30 MHz. Typical infrared molecular absorption lines in the low pressure (Doppler) limit also have widths (full width at half maximum) within this range.

Minimization of interference fringe effects has been carried out using several approaches. Complex wavelength modulation methods such as disclosed in Reid, et al., "Sensitivity Limits of Tunable Diode Laser Spectrometer, with Application to the Detection of $NO_2$ at the 100-ppt Level" (Appl. Opt. 19, 3349 (1980)); and Cassidy, et al., "Harmonic Detection with Tunable Diode Lasers - Two-Tone Modulation" (Appl. Phys. B 29, 279 (1982)) have been used. Such methods discriminate between fringes and absorption lines only when a difference exists between the characteristic widths of the fringes and the absorption lines. Furthermore, such laser modulation methods are specific to a particular laser or particular measurement and may require modification for lasers having different wavelength tuning properties or gas absorption lines having different widths.

Another approach to minimizing the effects of interference fringes is to perform successive measurements, one with the gas to be measured present and one with the gas removed, subtracting one scan from the other to obtain only the absorption spectrum of the gas. Removal of the gas may not be practical in many situations, such as on-line measurements of chemical processes, in situ measurements of atmospheric species, and the like. Even slight changes in the index of refraction of the gas mixture or the temperature of the system can shift the position of the fringes relative to the absolute laser frequency between laser wavelength scans. In addition, such approaches at least double the measurement time and require post-measurement processing of the data.

Yet another approach for minimizing interference fringe effects has been described in Webster, "Brewster-Plate Spoiler: A Nevel Method for Reducing the Amplitude of Interference Fringes that Limit Tunable-Laser Absorption," J.Opt. Soc. Am. B 2, 1464 (1985), and U.S. Pat. No. 4,684,258. Webster positions a transmissive plate in the beam path approximately at Brewster's angle between the optical surfaces which give rise to the interference fringes. Webster angularly oscillates the transmissive plate about Brewster's angle which, in effect, continuously varies the optical path length between the fringe-forming optical surfaces, thereby reducing the fringes on a time-averaged basis. The Webster device has several disadvantages and is not practical when the interference fringes are formed within a multiple pass cell. One major disadvantage is that an additional element must be introduced into the optical path. This greatly increases overall transmission losses within a system. The Brewster plate surfaces can also scatter laser light, thereby causing new fringes to be formed. This is quite likely if the plate is inserted into the path in a region where the laser beam diameter is large, that is, where the laser beam intercepts a significant fraction of the area of the plate. The plate additionally causes substantial displacement of the beam, unless the plate is very thin. Most infrared transmissive materials, such as calcium flouride and KRS-5, are readily available only in thicknesses greater than 3 mm. Plates of such thickness create beam displacements on the order of 1 mm or greater. In addition, because the index of refraction of such a plate varies as a function of wavelength, the orientation of the plate or the plate material itself will need to be changed if the laser wavelength is changed sufficiently.

The Brewster plate method of Webster is especially impractical for use in multiple pass cell systems. To reduce fringes generated by such a cell, a Brewster plate would have to be positioned inside the cell, between its multipass mirrors. In many measurement applications, such cells are vacuum tight and are operated at reduced pressure. Thus, mounting and controlling a Brewster plate within such a cell would pose design complications. For some applications, such as in situ monitoring of chemical processes, placement of any foreign element within a multipass cell may be entirely infeasible. In addition, in typical standard multipass cell designs such as "White" cells and "Herriott" cells, the various traverses of the cell by the laser beam are not confined to a small transverse area. Therefore, a Brewster plate would need to be similar in size to the multipass mirrors to ensure interception by the plate of all traverses of the cell. Scattering of laser light from such a large surface to one or more of the multipass mirrors is highly probable. Such scattering would create additional unwanted interference fringes which could not be eliminated by oscillating the plate.

Another significant disadvantage of using a Brewster plate in a multiple pass cell is that introduction of the Brewster element results in significant and unacceptable transmission losses, especially when used with randomly polarized laser beams. The transmission through such an element after n passes is $T = T_o^n$, where $T_o$ is the single pass transmission of the plate. If this single pass transmission is 80%, which is typical for infrared transmitting materials, after 40 passes, $T = (0.8)^{40} = 1.3 \times 10^{-4}$. Hence, only about 0.01 percent of the available light is transmitted through the cell, creating a severe loss of sensitivity in most cases. Even if 99% single pass transmission is achieved by the use of antireflection coatings, the net transmission after 40 passes is reduced by $\frac{2}{3}$, substantially compromising sensitivity in most applications.

One object of the present invention is to eliminate interference fringes and thereby substantially increase sensitivity in laser absorption measurements.

Another object of the invention is to increase detection sensitivity in multiple pass cell laser absorption measurement systems.

One advantage of the instant invention is that in accordance therewith, sensitivity of selected laser detection systems is sufficiently enhanced to enable their use in detecting the presence of substances previously undetectable using such systems.

Other objects, advantages and novel features, and further scope of applicability of the present invention will be set forth in part in the detailed description to follow, taken in conjunction with the accompanying drawing, and in part will become apparent to those skilled in the art upon examination of the following, or may be learned by practice of the invention. The objects and advantages of the invention may be realized and attained by means of the instrumentalities and combinations particularly pointed out in the appended claims.

SUMMARY OF THE INVENTION

In accordance with the present invention, there is provided an apparatus and method for improving the detection sensitivity of a laser absorption measurement system by overcoming optical interference effects, the system utilizing laser absorption for detecting gas phase atoms and molecular species within a gaseous medium. The system comprises a source for a laser beam. The coherence length of the laser source is at least equal to the distance between any fringe creating optical elements within the system, which contains at least one active optical element. Physical translational vibration is generated within the active optical element. The amplitude and frequency of the vibration produced are controlled to substantially eliminate fringes produced by the fringe producing elements. The frequency at which the optical element is vibrated is preferably asynchronous to any other modulation frequency used in the system. The amplitude or distance traversed by the element is preferably sufficient to cause a change in optical path length which corresponds to frequency tuning at least greater than one half of the fringe free spectral range. This corresponds to a distance greater than one quarter wavelength, the actual optical element movement amplitude preferably exceeding several wavelengths. Optical elements used comprise mirrors, lenses and the like. A mirror may be used as the active optical element, and may be either one of the elements which is producing the fringes or a separate mirror which is located within the optical path bounded by the fringe-forming elements. If a lens or other transmissive optical component is used as the active element, then this component is most preferably one of the elements which is causing the fringes. Optical element vibration is preferably generated using a piezoelectric transducer. Amplitudes used are from one-quarter to several wavelengths of the laser light and frequencies used are from a few (less than 10) Hz to an upper limit set by the frequency response of the piezoelectric transducer or other vibration-inducing device.

BRIEF DESCRIPTION OF THE DRAWINGS

The accompanying drawings, which are incorporated into and form a part of the specification, illustrate a preferred embodiment of the present invention and, together with the description, serve to explain the principles of the invention.

DETAILED DESCRIPTION OF A PREFERRED EMBODIMENT OF THE INVENTION

The apparatus and method of the present invention utilize translational oscillation or vibration of an active optical element. Although a preferred embodiment of the invention, as described herein, is applied to a mirror in a multiple pass cell, the use of the invention is not limited thereto. The preferred embodiment illustrated can be used, for example, in applications, such as in atmospheric trace species monitoring, pollutant monitoring, process control, combustion studies, and the like. Such applications usually utilize multiple pass devices in order to provide long interaction distances within the gas of interest, yet keep the physical length of the measuring device reasonable. The preferred embodiment illustrated is particularly useful in absorption and Raman scattering measurements where the effect is too weak for detection in a single pass of a cell, but where good signal to noise ratios can be obtained within from about 10 to about 100 passes. Those skilled in the art will recognize that even in such multiple pass cells, the total light absorbed or scattered will be a small fraction of the total intensity of the beam and that all sources of noise and interfering background signals should be minimized for satisfactory results to be obtained.

High detection sensitivity laser absorption systems include dual-beam normalization, harmonic detection and single and two-tone frequency modulation systems. Many such systems successfully minimize laser source noise and background fluctuations. However, unintended and unwanted Fabry-Perot fringes frequently appear in the beam in such systems within the optical path between its source and its detector. Such fringes almost always occur in multiple pass systems due to interference between overlapping laser beams at the mirror. Such fringes are well known to the practitioners of the art.

Figure 1:
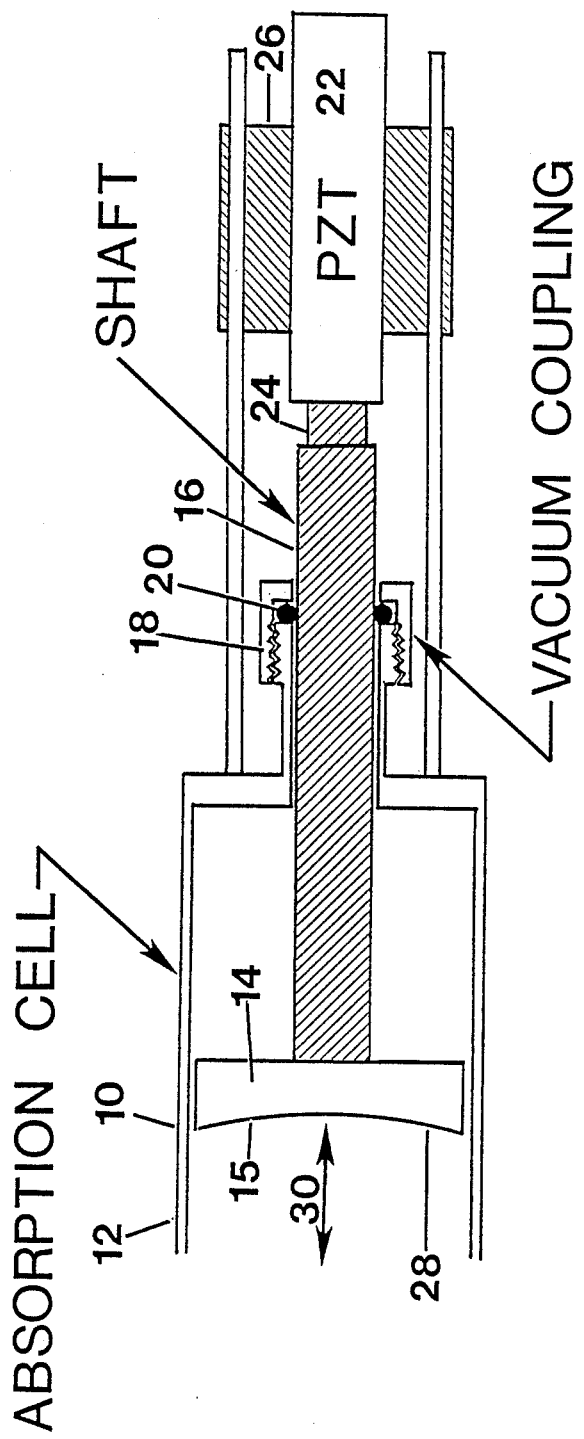
FIG. 1 illustrates a preferred embodiment of the invention.

Reference is now made to FIG. 1 which shows a preferred embodiment of the invention which can be used in such a system. As seen therein, the reflective end 10 of an absorption cell 12 comprises a mirror 14, having a reflective surface 15, affixed to a shaft 16 passing through a vacuum coupling 18 having an 0-ring seal 20. A piezoelectric transducer, or PZT, 22 disposed within a mount 26 allowing a translational vibration or oscillation, operatively communicates with shaft 16 through element 24. PZT 22 is oscillated using conventional electrical frequency and amplitude controls. A user can adjust the amplitude or translational length and the frequency of PZT movement and thereby, the amplitude or translational movement length, as represented by double-headed arrow 30, and frequency of mirror 14 which moves translationally in response thereto. Mirror 14 is either disposed within or bounds an optical fringe region.

In practicing the invention, the frequency at which the active optical element, such as mirror 14, is vibrated is selected to be asynchronous with respect to any other modulation frequencies used in the system. Thus, the instantaneous optical separation (L) of the fringe-forming surfaces is randomized relative to other characteristic frequencies of the system. Since the fringe spacing, or free spectral range, is directly proportional to 1/L, the spacing of the fringes is randomized in time. Thus, the fringes can be averaged over time to zero. Averaging is most effective if a sawtooth (triangle) waveform is used to drive the piezoelectric transducer that vibrates the optical element, so that each spatial position of the element is sampled with equal probability.

The fringe averaging effect may be obtained, for example, with a detection apparatus employing a lock-in amplifier referenced to a system modulation frequency which is asynchronous with respect to the vibration frequency of the active optical element. With such a design, the time required to tune the laser wavelength across one fringe contains many vibration periods of the active element, and the fringe amplitudes are averaged to zero. The most important consideration in choosing the vibration frequency of the active element is that it be asynchronous with other system frequencies, particularly the lock-in reference frequency, so that fringe averaging can occur.

The desired fringe averaging effect can alternatively be implemented without using a lock-in amplifier. The signals obtained from very rapid repetitive scans of the laser wavelength across the desired spectral interval are averaged by, for example, a digital signal averager. The laser scan repetition frequency is chosen to be much faster than the vibration frequency of the fringe-averaging optical element. Thus, fringes may appear in the detected signal in each separate sweep of the laser wavelength, but the fringe separation varies from sweep to sweep, and fringe amplitudes are averaged to zero by averaging the signal from many sweeps. Again, the desired averaging effect is obtained because the vibration frequency of the active optical element is asynchronous with respect to other system frequencies, in this case the sweep frequency of the laser.

Interference fringes are substantially eliminated when the translational movement of the mirror tunes the cavity by at least one-half the fringes' free spectral range, which corresponds to a movement greater than one-quarter of the laser wavelength. In practicing the invention using the preferred embodiment disclosed herein, the distance traversed by mirror 14 actually exceeds several beam wavelengths.

One advantage of practicing the invention is that if mirror 14 has a broadband reflective coating 28, fringe reduction is effective over a large band of beam wavelengths. The angularly oscillating Brewster plates used in the prior art, on the other hand, must be individually set for a single wavelength in terms of transmission, index of refraction, and tilt. Too, mirror 14 inherently works with beams of various diameters whereas a Brewster plate device is limited to use with a narrowly focused beam so that beam steering and misalignment effects are small.

Figure 2:
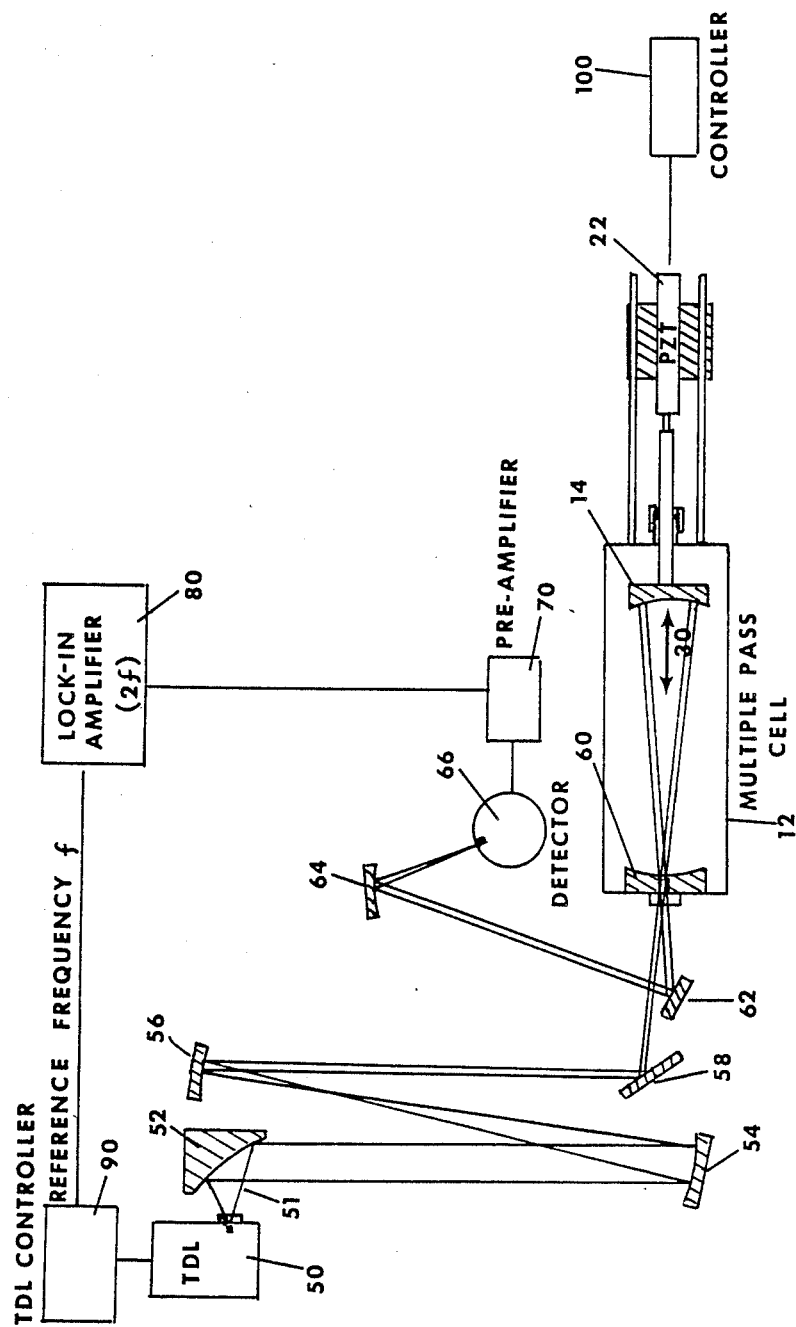
FIG. 2 is a schematic diagram of a laser absorption system employing the preferred embodiment of the invention in a multiple pass cell.

FIG. 2 shows a schematic of one preferred embodiment of the invention used in a particular laser absorption apparatus. A single mode lead-salt diode laser 50, such as model TDL-1270-N-OS1 available from Fujitsu, which is tunable in the wavelength region near 7.9 microns (1266 cm$^{-1}$) is used in combination with a multiple pass absorption cell 12, employing an active mirror 14, which can be longitudinally vibrated in accordance with the invention, and a HgCdTe photovoltaic detector 66, such as model MPV11-.1-B60, available from New England Research Corporation. The multiple pass cell 12 can be a Herriott design, formed by a spherical mirror 60 and the active mirror 14. In the FIG. 2 apparatus, longitudinal vibration of the active mirror 14 is primarily intended to eliminate interference fringes arising in the multiple pass cell 12 where mirror 14 is a bounding element of the fringe-forming region, but such vibration would also be effective in removing fringes which may occur in other optical regions of the system, provided that mirror 14 is contained within the fringe-forming region. The optical path of a beam 51 from laser 50 is established using mirrors 52, 54, 56, and 58. Mirrors 62 and 64 collect the laser light transmitted from cell 12 to the detector 66. Clearly, the design shown in the schematic is only one of many possible optical layouts for practicing the invention.

The vibration of mirror 14 is driven by a piezoelectric transducer 22, such as a Polytek Optronics Model P173, and controlled by a controller 100, which may comprise, for example, a Polytek Optronics P-265 high voltage controller and a Wavetek function generator. The function generator controls the type of waveform provided, preferably a triangle wave, the frequency, and the amplitude used to vibrate the mirror. The wavelength of diode laser 50 can be tuned and modulated by a module 90, such as a Spectra-Physics SP-5820 laser control module which slowly ramps the laser current to tune the laser wavelength, while superimposing a small 1 kHz modulation of frequency f on the laser current. The output signal from detector 66 is amplified by a preamplifier 70 and then sent to a lock-in amplifier 80, such as a Stanford Research Systems SR530. The lock-in amplifier 80 is referenced to frequency 2f, such that the output is a "second harmonic" signal which approximates the second derivative of the absorption line.

Figure 3:
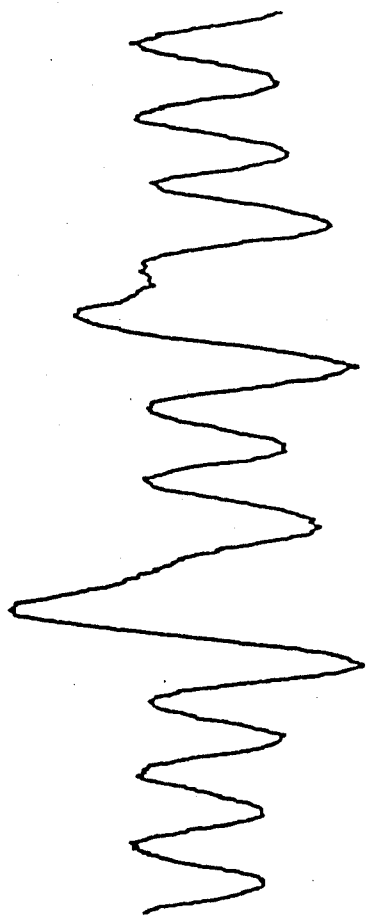
FIG. 3 shows an output spectrum in the absence of application of fringe reduction in accordance with the invention.
Figure 4:
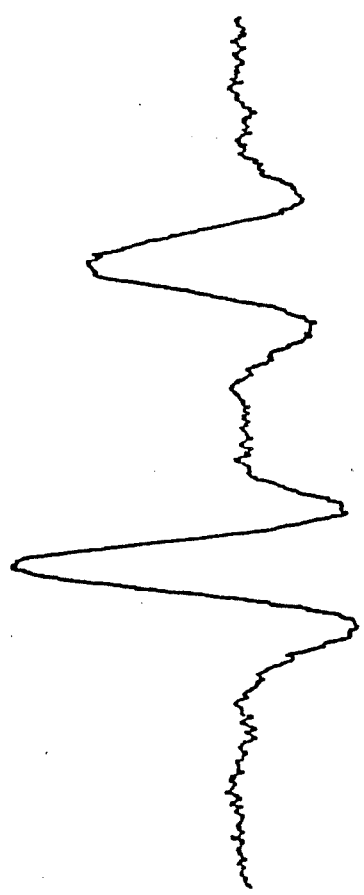
FIG. 4 shows the spectrum of FIG. 3 when fringe reduction is applied in accordance with the invention.

In order to demonstrate the effectiveness of the invention in eliminating unwanted interference fringes in laser absorption spectra, second harmonic absorption scans of naturally occurring nitrous oxide ($N_2O$) in sampled ambient room air were made using the apparatus shown in FIG. 2. For these experiments, room air was continuously pumped through cell 12 using a vacuum pump, such that the pressure inside the cell was 10.5 Torr. Absorption scans obtained in these experiments are shown in FIGS. 3 and 4. FIG. 3 shows an output spectrum when mirror 14 was not vibrated and FIG. 4 shows the same spectrum when translational vibration was applied to mirror 14. For the data in FIG. 4, the mirror was traversed over a distance of about 40 microns, which corresponds to approximately 5 wavelengths, at a frequency of 23 Hz. All other conditions for the two scans were identical. In FIG. 4 two absorption lines are evident, the first line being an absorption line of $N_2O$ at 1265.6638 cm$^{-1}$. The second line arises from a different atmospheric species, believed to be $CO_2$. In FIG. 3, the absorption lines are substantially obscured by interference fringes. By calibration of the laser tuning rate using known gas absorption lines, the fringe spacing was found to be consistent with a fringe-forming optical path corresponding to one round trip in the multiple pass cell.

FIGS. 3 and 4 clearly show the effectiveness of the invention using a PZT-driven mirror in averaging the unwanted interference fringes. The amplitude of the $N_2O$ signal corresponds to an absorption of 0.3%. The amplitude of the fringes with the mirror vibration turned off is equivalent to about 0.1% absorption and clearly prevents any accurate measurement of the absorption lines shown. The base line noise with fringe averaging on corresponds to about 0.008% absorption, within a factor of two of the thermal noise of the detector in this case. Even on an expanded scale, no evidence of any residual fringes was observed when longitudinal vibration of the mirror was applied. The fringe averaging method and apparatus was effective in this design at modulation frequencies up to about 100 Hz, above which the excursion range of the PZT falls off with frequency.

In this experimental example, the $N_2O$ signal corresponds to naturally occurring $N_2O$ in the atmosphere, which from many previous measurements is known to have a concentration of approximately 300 ppb. Without fringe averaging, the minimum detectable concentration is certainly not less than one third of this value, or 100 ppb. With fringe averaging, the noise level of 0.008% absorption is equivalent to a concentration of $N_2O$ of approximately 8 ppb. Thus, the sensitivity of the FIG. 2 apparatus for detection and accurate measurement of atmospheric $N_2O$ is improved dramatically by the use of the invention. Similar improvements would be obtained for any other gas phase species that can be measured by laser absorption.

The invention can be embodied into many of the common detection schemes used in laser absorption spectroscopy, including: direct measurement of laser transmission, such as in systems using mechanical beam chopping and detection with lock-in amplifiers, derivative or harmonic detection systems utilizing laser wavelength modulation at moderate frequencies, typically below 1 MHz, and detection at the modulation frequency or a harmonic of the modulation frequency using a lock-in amplifier or other phase-sensitive detector, frequency modulation (FM) or optical heterodyne spectroscopy using laser wavelength modulation at one or more high frequencies, typically greater than 1 MHz, and detection using phase-sensitive demodulation, and sweep integration or signal averaging systems, utilizing repetitive tuning of the laser tuning sweeps. Signal averaging might be used in combination with direct transmission, derivative or harmonic or frequency modulation.

The invention can also be embodied in dual beam detection systems, which split the laser beam and detect both a signal and a reference beam, subsequently electronically or digitally processing the two channels to minimize background and laser noise effects.

The invention can also be embodied in optical measurement systems using a coherent light source, including Raman scattering, multiphoton (originating from one or more lasers) absorption and scattering processes and in systems employing counterpropagating laser beams.

The invention can be practiced with both pulsed and cw lasers, as long as the coherence length of the output is comparable to or greater than the distance between potential fringe-forming optical elements in the system.

The invention can be practiced in all spectral regions from the far infrared to the vacuum ultraviolet.

Although the invention has been described with reference to these preferred embodiments, other embodiments can achieve the same results. Variations and modifications of the present invention will be obvious to those skilled in the art and it is intended to cover in the appended claims all such modifications and equivalents.

What is claimed is:

1. In a system utilizing laser absorption for detecting gas phase atoms and molecular species within a gaseous medium, the system comprising a source for a laser beam, the coherence length of the laser source being at least equal to the distance between any fringe creating optical elements within the system, an apparatus for improving the detection sensitivity of the system by overcoming optical interference effects comprising:
   an active optical element disposed on an optical path in said system;
   means for generating, along said optical path, physical translational vibration within said active optical element; and
   means for controlling the amplitude and frequency of said vibration producing means to substantially eliminate fringes produced by the fringe producing optical elements.

2. The invention of claim 1 wherein said active optical element comprises a mirror.

3. The invention of claim 1 wherein said active optical element comprises a lens.

4. The invention of claim 1 wherein said vibration generating means comprises a piezoelectric transducer.

5. The invention of claim 1 wherein said controlling means comprises means for controlling amplitude between about one-quarter wavelength and about ten wavelengths.

6. The invention of claim 1 wherein said controlling means comprises means for controlling frequency between about 5 Hz and the upper vibrational limit of the vibration producing means.

7. The invention of claim 1 wherein said controlling means operates said translational vibration generating means at a frequency asynchronous to any other modulation frequency within the system.

8. The invention of claim 1 wherein said controlling means operate said translational vibration generating means to vibrate said active optical element a translational distance sufficient to cause a change in optical path length at least greater than one-quarter wavelength, equivalent to frequency tuning of at least one-half the fringe free spectral range.

9. The invention of claim 1 wherein said controlling means operates said translational vibration generating means to vibrate said active optical element a distance exceeding several beam wavelengths.

10. In a system utilizing laser absorption for detecting gas phase atoms and molecular species within a gaseous medium, the system comprising a source for a laser beam, the coherence length of the laser source being at least equal to the distance between any fringe creating optical elements within the system, the system comprising an optical path having an active optical element disposed therein, a method for improving the detection sensitivity of the system by overcoming optical interference effects comprising:
   generating, along the optical path, physical translational vibration within the active optical element; and
   controlling the amplitude and frequency of the vibration produced to substantially eliminate fringes produced by the fringe producing optical element.

11. The method of claim 10 further comprising controlling the frequency of the vibration produced to be asynchronous to any other modulation frequency used in the system.

12. The method of claim 10 further comprising controlling the amplitude of the vibration produced to cause a change in the optical path length at least greater than one-quarter wavelength, equivalent to frequency tuning greater than one-half of the fringe free spectral range.

* * * * *